United States Patent [19]

Jenkinson

[11] Patent Number: 4,889,490

[45] Date of Patent: Dec. 26, 1989

[54] DENTAL MASK

[76] Inventor: Jeffrey A. Jenkinson, Rte. 2 Keoway Village Apartments, Apt. F-3, Seneca, S.C. 29678

[21] Appl. No.: 155,126

[22] Filed: Feb. 11, 1988

[51] Int. Cl.$^4$ .............................................. A61C 5/14
[52] U.S. Cl. .................................................. 433/136
[58] Field of Search ................... 433/136, 137; 128/12

[56] References Cited

U.S. PATENT DOCUMENTS

| | | | |
|---|---|---|---|
| 1,774,285 | 8/1930 | Middaugh | 433/137 |
| 4,344,758 | 8/1982 | Wielhouwer | 433/136 |
| 4,512,742 | 4/1985 | Shanel | 433/136 |
| 4,664,628 | 5/1987 | Totaro | 433/136 |

OTHER PUBLICATIONS

Denticator X-Spand, Cheek and Lip Retractor, 107 Park Lane, Brisbane, Calif. 94005, May 1984.

Primary Examiner—Robert Peshock
Attorney, Agent, or Firm—Cort Flint

[57] ABSTRACT

A dental mask (A) is disclosed for protecting the facial area of a dental patient during dental work. The mask includes a mask frame (B) and a protective sheet (C). Latex (24) is used for protective sheet (C) having a medial opening (36) which fits about cheek retractors (12, 14) of mask frame (B). Support arms (26, 28, 30, and 20) support protective sheet (C) in a generally taut condition when the cheek retractors are inserted and retract the cheeks to expose an oral cavity (22) of the patient during dental work. Protective sheet (C) protects the surrounding facial area of the oral cavity, is inclined to provide proper breathing through the nose, and shields the eye area (42) against airborne contaminant particles which are likewise prevented from being deposited on the facial area of the patient.

19 Claims, 3 Drawing Sheets

DENTAL MASK

BACKGROUND OF THE INVENTION

The invention relates to the field of dentistry, and more particularly to a dental mask which retracts the cheeks to open the oral cavity for access during dental procedures, and which protects the patient's facial area during dental work.

In the past, cheek retraction devices have been known for use in photography. For example, in orthodontics the cheek retractor is inserted to photograph the teeth before and after orthodontic work. One dental photographic mask is manufactured by Hager & Werken GmbH of Duisburg, Germany, and sold under the name Spandex. This device includes a plastic flexible mouth piece which has a curved cheek retractor that flexes and collapses to fit into the mouth. When the collapsed device is let go it retracts. During retraction the cheeks are retracted exposing the teeth and oral cavity for photography. Protective devices commonly referred to as a rubber dam have been used in dental work. The rubber dam consists of a sheet of latex material. A hole is punctured in the latex material and the latex is fitted over one or more teeth. A metal clamp is used to slide the latex material over the tooth or teeth. The outside of the latex sheet is carried by a wire frame to which latex is attached by prongs. The metal frame is loose and laid upon the patient's face while the latex serves as a working envelope for access to the area of the patient's oral cavity where work is to be performed. The latex acts like a barrier and prevents materials from going down the patient's throat. Napkins have also been used to cover a facial area of the patients. Numerous types of devices have been proposed for holding the napkins like elastic head bands, for example.

No method or device has been proposed which is entirely satisfactory for retracting the cheeks of the patient for access to the oral cavity and to cover the surrounding facial area during dental work in an effective manner. There are many procedures performed under dental work which cause contaminants to be sprayed upon the patient's face. For example, a popular teeth cleaning process includes spraying baking soda against the teeth to blast the stains and polish the teeth. This causes contaminant particles including baking soda and water to spray in the air around the patient's face and be deposited on the patient's face. If the face becomes too dirty, the face must be cleaned. Often facial make-up must be replaced. In the case of patient's with contact lenses, it is recommended that the eyes be closed during this procedure so that the soda dust and other particulate matter does not enter the eyes. Sonic scaler devices are also utilized in dental work which vibrate at sonic frequencies and spray water. These devices also cause water spray and loose particulate matter from the teeth to become sprayed in the air and deposited on the patient's face. Numerous other procedures in dental work using instruments vibrating or operating at high speeds cause foreign or contaminant matter to be sprayed into the air adjacent the patient's face and deposited.

Accordingly, an object of the invention is to provide a dental mask for protecting a patient's face against airborne particulate and contaminant matter during dental work.

Another object of the invention is to provide a device for retracting the cheeks and for covering the facial area surrounding the oral cavity of a dental patient during dental work.

Another object of the invention is to provide a device which retracts the cheeks, covers the surrounding facial area of a dental patient, and aids in the retention of particulate and contaminant matter resulting from the dental procedure within the more open oral cavity while protecting the facial area against any airborne particulate or contaminant matter.

SUMMARY OF THE INVENTION

The above objectives are accomplished according to the invention by providing a dental mask device adapted for insertion in the oral cavity of a dental patient and for supporting a protective sheet covering a surrounding facial area of the patient while retracting the patient's cheeks. The device consists of a mask frame having a pair of movable cheek retractors for retracting the left cheek and right cheek of the dental patient. There is lateral support carried by the sides of the mask frame for attaching and supporting opposing sides of the protective sheet to cover the facial area of the patient in a generally taut condition. An upper support supports an upper side of the protective sheet in a taut condition; and lower support supports a lower side of the protective sheet in a generally taut condition. Attachment barbs are carried by each support means for attaching the protective sheet to the mask frame. The upper support includes vertically inclined support arms for supporting the protective sheet at an inclined position relative to the patient's facial area when the dental mask is fitted inside the patient's oral cavity. With the mask held in this manner, airborne contaminants and particles are deflected from the area of the patient's eyes while the patient's nose is left unobstructed for breathing.

DESCRIPTION OF THE DRAWINGS

The construction designed to carry out the invention will hereinafter be described, together with other features thereof. The invention will be more readily understood from a reading of the following specification and by reference to he accompanying drawings forming a part thereof, wherein an example of the invention is shown and wherein.

DESCRIPTION OF A PREFERRED EMBODIMENT

Figure 1:
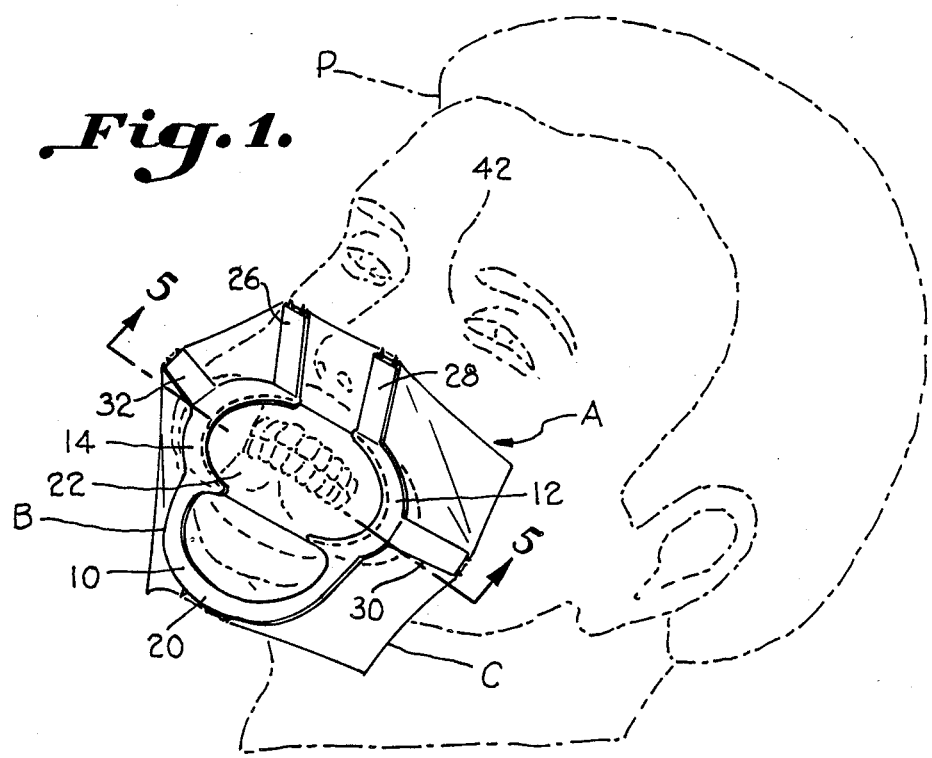
FIG. 1 is a perspective view illustrating a dental patient with a dental mask according to the invention.

Referring now in more detail to the drawings, FIG. 1 illustrates a dental mask device, designated generally as A, constructed in accordance with the present invention which includes a mask frame B made from a suitable resilient plastic and a protective sheet C carried by frame B. Dental mask frame B includes a flexible frame 10 which includes a left cheek retractor 12 and a right cheek retractor 14, as viewed relative to the patient. Frame 10 may be made from any suitable resilient plastic material.

Figure 3:
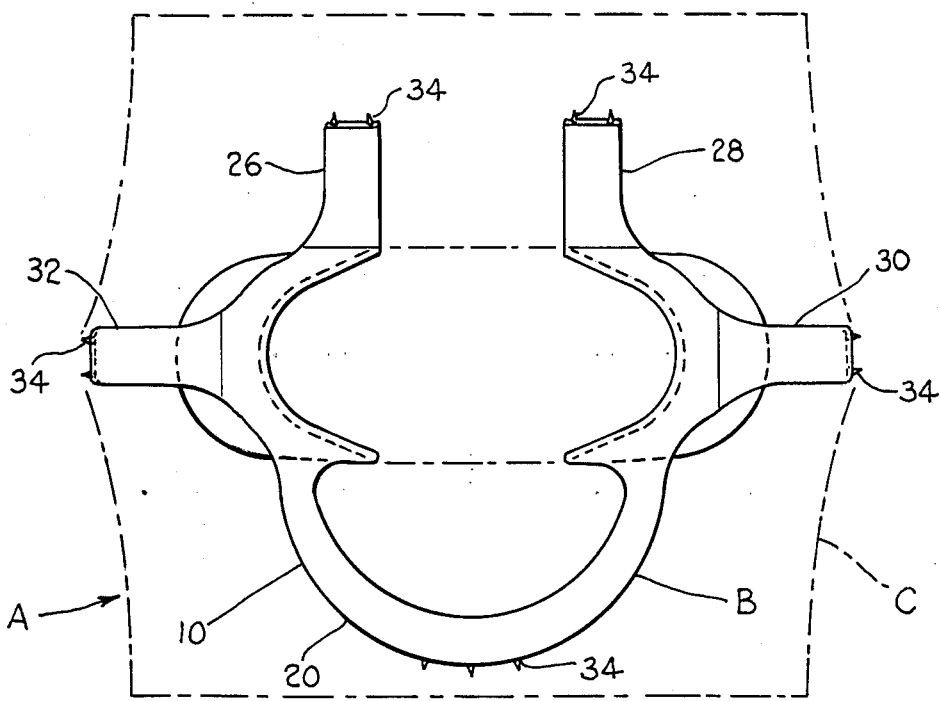
FIG. 3 is a front plan view of a dental mask constructed according to the invention.
Figure 5:
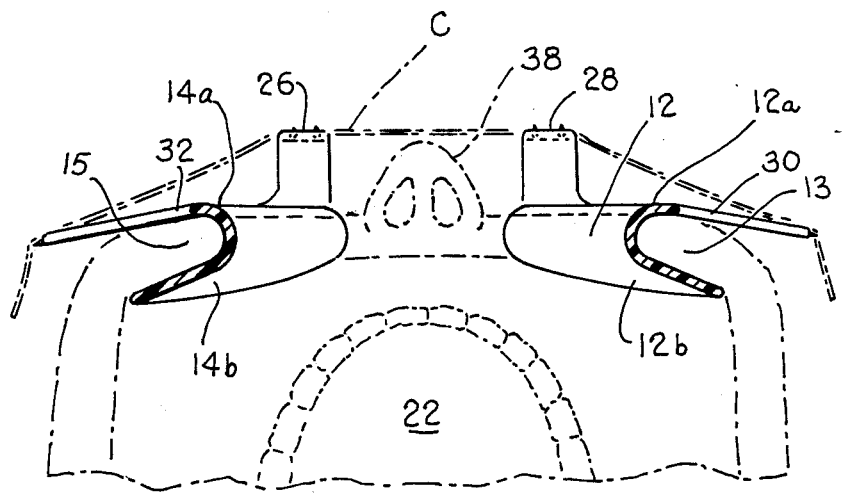
FIG. 5 is a sectional view taken along line 5—5 of FIG. 1.

As can best be seen in FIGS. 3 and 5, left cheek retractor 12 includes a cheek receiving flange opening 13 defined by a front flange 12a and flange 12b. Right cheek retractor 14 includes a cheek receiving flange opening 15 defined by a front flange 14a and a rear flange 14b. Dental mask frame 10 is flexible and includes a pincerlike bridge 20 which connects left and right cheek retractors 12 and 14. By pinching the arms of bridge 20, left and right cheek retractors collapse and come together so that the same may be fitted within the oral cavity 22 of the patient's teeth. When the arms of the bridge are released, the left and right cheek retractors move away from each other retracting the left and right cheeks of the patient leaving the oral cavity open for dental work. The frame and cheek retractors may be in a number of suitable forms and are illustrated in the form of the Spandex photography mask described in the background.

Figure 6:
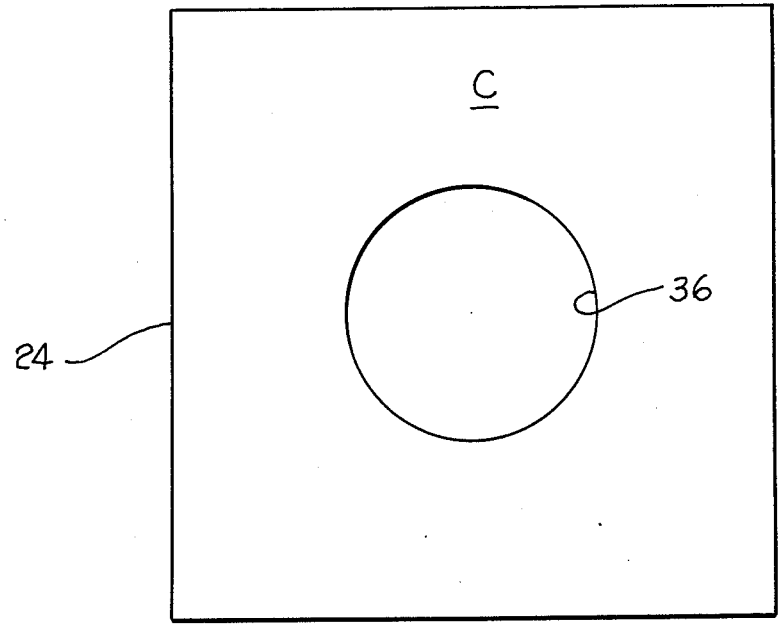
FIG. 6 is an elevation of a protective latex sheet for a dental mask in accordance with the invention.

Referring now in more detail to the invention, FIGS. 1 and 3 show a protective sheet C in the form of a rectangular sheet 24 of suitable sanitary material such as latex. Support means for attaching latex sheet 24 to mask frame B is illustrated in the form of a plurality of support arms 26, 28, 30, and 32, and bridge arm 20. Each arm includes a plurality of plastic barbs 34 which may engage and penetrate latex sheet 24 including a plurality of plastic barbs 34 on the end of bridge 20. The support arms are located around mask frame 10 so that latex sheet 24 is maintained in a stretched out generally rectangular configuration effectively covering and protecting the facial area of patient P surrounding the oral cavity 22. As can best be seen in FIG. 6, latex sheet 24 includes a central opening 36 which is also fitted inside the flange openings 13 and 15 and retained by cheek retractors 12 and 14. The central opening 36 of latex sheet 24 contracts and expands as the cheek retractors flex and reflex.

Figure 2:
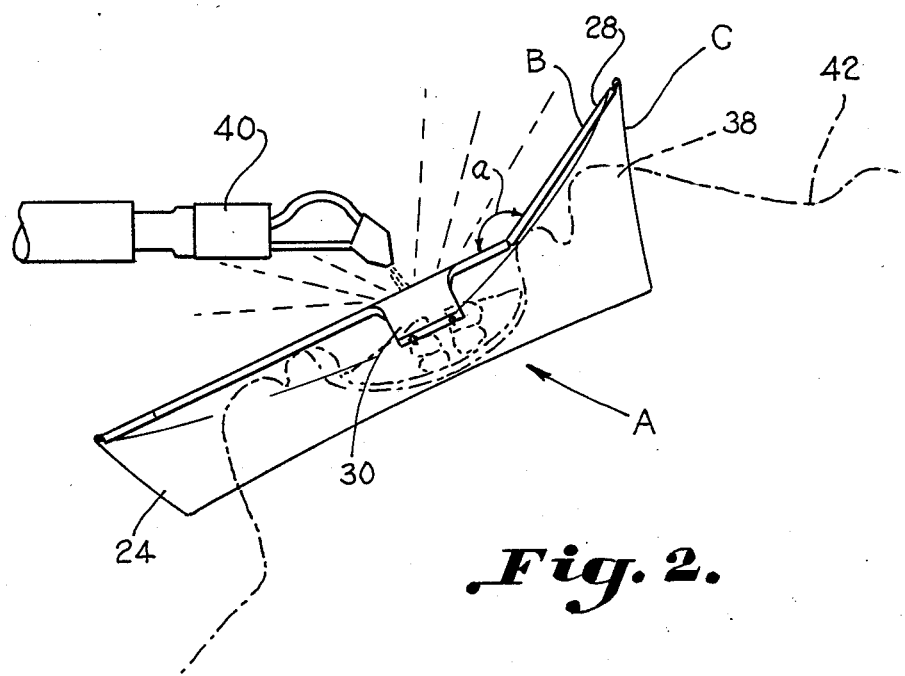
FIG. 2 is a side elevation of a dental patient wearing a dental mask in accordance with the invention undergoing dental hygiene with an air polish instrument.
Figure 4:
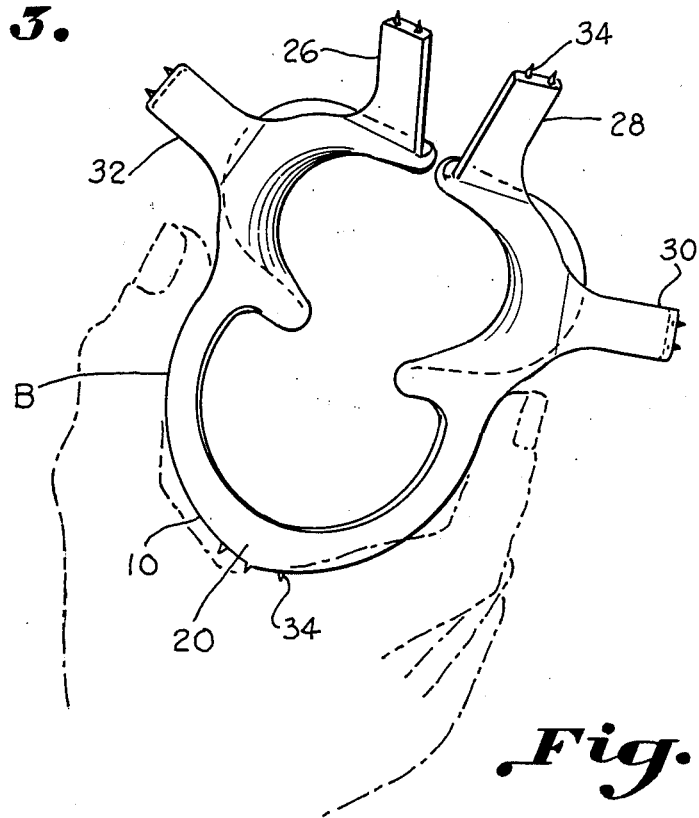
FIG. 4 is a perspective view of the dental mask of FIG. 3 flexed in a collapsed position for insertion into an oral cavity.

As can best be seen in FIG. 2 and 5, upper support arms 26 and 28 are carried at free ends 10a and 10b of frame 10 and are inclined outwardly at an angle "a" of about 60 degrees with respect to the frame. The latex flexes with the frame as the free ends converge like in FIG. 4. In this configuration, latex sheet C is held away from the nose 38 of the patient so that the nose is unobstructed for proper breathing. It is also important to note that at this angle or other proper inclination, support arms 26 and 28 provide a means for holding latex sheeting at such an angle that contaminant particles and other airborne matter caused by polishing instrument 40 are deflected effectively from the eye area 42 of the patient during dental work, as can best be seen in FIG. 2.

While a preferred embodiment of the invention has been described using specific terms, such description is for illustrative purposes only, and it is to be understood that changes and variations may be made without departing from the spirit or scope of the following claims.

What is claimed is:

1. A dental mask device adapted for insertion in the oral cavity of a dental patient for supporting a protective sheet covering a surrounding facial area of the patient for protection against contact by airbone contaminant particles and the like resulting from dental work while retracting the patient's cheeks, said device comprising:
   a flexible mask frame;
   a pair of cheek retractors carried by said mask frame which are pivotable within said oral cavity; and
   support means carried by said mask frame for attaching said protective sheet to said mask frame in a position that said patient's oral cavity is open for said dental work and the patient's nose is unobstructed for proper breathing while said facial area of said patient surrounding said open oral cavity is covered by the protective sheet to protect against deposition of said contaminant particles discharged from the oral cavity during dental work.

2. The device of claim 1, wherein said support means includes a plurality of barbs carried by said mask frame about a said facial area for attachment of said protective sheet.

3. The device of claim 2 including a plurality of outwardly extending support arms carried by said mask frame; and said barbs being carried adjacent the end of each said support arm.

4. The device of claim 3 including:
   a plurality of upper support arms carried adjacent an upper portion of said mask frame with barbs extending upwardly towards a nose area of said patient;
   a plurality of support arms extending laterally from said mask frame carrying barbs for attaching said protective sheet on the sides of said mask frame; and
   a plurality of lower barbs carried adjacent a lower portion of said mask frame in a manner that said protective sheet is retained in a generally taut condition over said facial area at an inclination to said nose area.

5. The device of claim 1, wherein said support means includes:
   a plurality of support arms carried by said mask frame which includes a pair of upwardly extending arms extending generally upwardly and outwardly from said frame on opposing sides of a nose of the patient; and
   attachment means carried by said support arms for attaching said protective sheet to said frame.

6. A dental mask device adapted for insertion in the oral cavity of a dental patient for supporting a protective sheet covering a surrounding facial area of the patient for protection against contact by airborne contaminant particles and the like resulting from dental work while retracting the patient's cheek, said device comprising:
   a flexible mask frame which is open at a portion of the frame defining a first free end and a second free end;
   a pair of cheek retractors carried by said flexible frame for retracting the left cheek and right cheek of the dental patient;
   retaining means carried by said cheek retractors about which an aperture in a portion of said protective sheet is fitted leaving said oral cavity open and exposed for said dental work while said protective sheet protects said surrounding facial area;
   lateral support means carried by the sides of said mask frame for attaching and supporting opposing sides of said protective sheet to cover said facial area of the patient in a generally taut condition;

upper support means for supporting an upper side of said protective sheet in said taut condition;

lower support means for supporting a lower side of said protective sheet in said generally taut condition; and attachment means carried by each said support means for attaching said protective sheet to said flexible mask frame.

7. The device of claim 6, wherein said upper support means includes vertically inclined support means for supporting said protective sheet at an inclined position relative to said patient's facial area when said dental mask is fitted inside the patient's oral cavity with cheeks retracted in a manner that airborne contaminants and particles are deflected from the area of the patient's eyes while the patient's nose is left unobstructed for breathing.

8. The device of claim 6, wherein said support means supports said protective sheet covering a facial area of the patient extending from slightly above the patient's nose to slightly below the patient's chin and covering laterally an area extending over both cheeks.

9. The device of claim 6 including a protective sheet of material having a central opening adapted to be received over said cheek retractors of said mask frame and having a lateral and longitudinal extent for attachment to said support means of said mask frame in a generally taut condition in a manner that as said frame may flex to insert into the patient's oral cavity, and said sheet contracts and then expands to a generally taut condition upon retraction of said patient's cheeks to serve as a generally tight protective covering over said facial area.

10. The device of claim 6, wherein said upper support means comprises:

a first inclined support extending outwardly from said first end of said mask frame;

a second inclined support extending outwardly from said second end of said mask frame; and said first and second inclined supports extending outwardly at an inclination to said mask frame for supporting said protective sheet at an inclination to said facial area which leaves the nose of the patient unobstructed for breathing and shields the eyes of the patient against airborne contaminants and particles.

11. The device of claim 10, wherein said first and second inclined supports are at an angle of about 60 degrees to said mask frame.

12. The device of claim 10, wherein said support means further includes:

a third support arm extending laterally from said mask frame over the left cheek of said patient for supporting said protective sheet over said left cheek; and a fourth support arm extending over the right cheek of said patient adapted for extending from said mask frame over the right cheek of said patient for supporting said protective sheet over said right cheek.

13. The device of claim 12, wherein said flexible frame includes a bridge portion connecting said third and fourth support arms which serves as a pincerlike element to collapse and retract said frame and said sheet retractors to respectively fit in said oral cavity and retract said cheeks; and a fifth support arm carried by said bridge portion in a manner that said protective sheet is supported on all four sides in a generally taut condition stretched over the facial area of the patient's face for protection.

14. A dental mask device adapted for insertion in the oral cavity of a dental patient for supporting a protective sheet covering a surrounding facial area of the patient for protection while retracting the patient's cheeks, said device comprising:

a dental mask frame;

a pair of moveable cheek retractors carried by said frame in a manner that said cheek retractors may be inserted into said oral cavity of the patient and be retained in said oral cavity with said cheeks of patient being retracted while supporting said mask frame over the facial area of said patient;

support means carried by said dental mask frame for supporting a protective sheet to cover said facial area of said patient;

upper support means for supporting an upper edge of said protective sheet above the oral cavity and adjacent the nose; and said upper support means supporting said protective sheet inclined outwardly from a plane of said dental mask frame for supporting said protective sheet at an inclination to the facial area for an unobstructed nose and proper breathing and to provide a shield for deflecting airborne contaminants and particles from the eyes of the patient during dental work.

15. The device of claim 14, wherein said support means comprises barbs carried by each side of said frame for supporting said protective sheet.

16. A method of protecting a surrounding area of an oral cavity of a dental patient against contact by airborne contaminant particles and the like during dental work comprising:

using a cheek retractor to retract the cheeks of said patient during said dental work; and supporting a protective sheet having a medial aperture covering the facial area of the dental patient on a frame common and integral with the cheek retractors so that the frame and protective sheet are held in place while the cheek retractor is inserted in the oral cavity properly positioning said protective sheet for covering said facial area while leaving said oral cavity open and exposed through said apertures for dental work.

17. The method of claim 16 including supporting said protective sheet on said frame at an inclination to the facial area and frame so that said protective sheet extends generally upwards towards the nose of the dental patient and sufficiently spaced from the nose for unobstructed breathing and shielding the eyes from airborne contaminant particles.

18. The method of claim 16 including attaching a resilient plastic sheet as a protective sheet to said frame and attaching said sheet in a generally stretched condition to said frame so that it is in a generally taut condition as a protective mask.

19. The method of claim 18 including using a flexible frame for supporting said resilient elastic sheet so that both flex to insert said cheek retractors into said oral cavity.

* * * * *